United States Patent [19]

Nojima et al.

[11] Patent Number: 4,935,520
[45] Date of Patent: Jun. 19, 1990

[54] COMPOUND, OLEYL-2-PYRIDINIOETHYL PHOSPHATE HAVING ANTIFUNGAL AND ANTIPROTOZOAL PROPERTIES

[75] Inventors: Shoshichi Nojima, Tokyo; Hiroaki Nomura, Osaka, both of Japan

[73] Assignee: Takeda Chemical Industries, Ltd., Osaka, Japan

[21] Appl. No.: 247,429

[22] Filed: Sep. 19, 1988

Related U.S. Application Data

[63] Continuation of Ser. No. 549,464, Nov. 7, 1983, abandoned.

[30] Foreign Application Priority Data

Nov. 8, 1982 [JP] Japan ................................. 57-196430

[51] Int. Cl.⁵ ............................ C07F 9/58; C07F 9/65
[52] U.S. Cl. ...................................... 546/22; 548/112; 544/157; 544/159; 544/337
[58] Field of Search .................. 546/22; 544/157, 159, 544/337

[56] References Cited

U.S. PATENT DOCUMENTS 4,426,525 1/1984 Hozumi et al. ...................... 546/22

Primary Examiner—Alan L. Rotman
Attorney, Agent, or Firm—Wegner & Bretschneider

[57] ABSTRACT

Phospholipids, inclusive of pharmaceutically acceptable salts thereof, of the formula

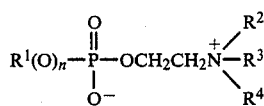

wherein $R^1$ is a $C_{8-30}$ aliphatic hydrocarbon residue, $R^2$, $R^3$ and $R^4$ are independently hydrogen or lower alkyl or

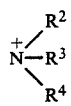

represents cyclic ammonio and n is 0 or 1, exhibit inhibitory activity to multiplication of tumor cells and antimycotic (antifungal) and antiprotozoal activities, and are useful for inhibiting multiplication of tumor cells and prolonging the survival time of tumor-bearing warm-blooded animal, for treating or preventing a disease in an animal caused by a mycete (fungus) and for treating or preventing a plant disease.

1 Claim, No Drawings

COMPOUND, OLEYL-2-PYRIDINIOETHYL PHOSPHATE HAVING ANTIFUNGAL AND ANTIPROTOZOAL PROPERTIES

This application is a continuation of Ser. No. 549,464, filed Nov. 7, 1983, abandoned.

This invention relates to novel antifungal and antitumor agents. More particularly, this invention relates to antifungal and antitumor agents containing a phospholipid, inclusive of a pharmaceutically acceptable salt thereof, of the formula

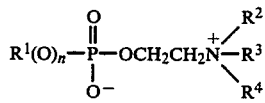
(I)

wherein $R^1$ is a $C_{8-30}$ aliphatic hydrocarbon residue, $R^2$, $R^3$ and $R^4$ are independently hydrogen or lower alkyl or

represents cyclic ammonio, and n is 0 or 1.

Referring to the above formula (I), the $C_{8-30}$ aliphatic hydrocarbon residue represented by $R^1$ includes straight or branched chain saturated or unsaturated aliphatic hydrocarbon residues (e.g. alkyl, alkenyl, alkynyl, etc.), which may be substituted or unsubstituted. The alkenyl group may be Z- or E-configuration. $R^1$ may have further one or more substituents such as hydroxy, mercapto, amino, oxo, carbamoyl, carboxy, halogen, $C_{3-7}$ cycloalkyl, $C_{3-7}$ cycloalkenyl, aryl (e.g. phenoxy, tolyl, phenyl, etc.), etc. As a preferred embodiment of $R^1$, there may be mentioned, for example, $C_{8-30}$ alkyl group [e.g. n-dodecyl, n-tridecyl, n-tetradecyl, 3,7,11-trimethyldodecyl, n-pentadecyl, n-heptadecyl, n-octadecyl, n-eicosyl, n-docosyl, 3,7-dimethyloctyl, (1-octyl)nonyl 3,7,11,15-tetramethylhexadecyl], among which $C_{10-30}$ alkyl group is more preferred, $C_{8-30}$ alkenyl group [e.g. 8-tridecenyl ($\Delta^8$), 3,7,11-trimethyl-2,6,10-dodecatrienyl, 8-tetradecenyl ($\Delta^8$), 8,11-tetradecadienyl ($\Delta^{8,11}$), 8-heptadecenyl ($\Delta^8$), 2-octadecenyl, 9-octadecenyl (oleyl), 9,15-octadecadienyl, 9,12,15-octadecatrienyl, 8,11,14-heptadecatrienyl ($\Delta^{8,11,14}$), 8,11-octadecadienyl ($\Delta^{8,11}$), 4,7,10,13-nonadecatetraenyl ($\Delta^{4,7,10,13}$), phythyl, 3,7,11,15-tetramethyl-2,6,10,14-hexadecatetraenyl, 3,7,11,15-tetramethyl-2,4,6,10,14-hexadecapentaenyl, 12-(2,3-cyclopentenyl)dodecyl, 12-(2,3-cyclopentenyl)-5-dodecenyl, 11-hydroxy-8-heptadecenyl, 3,7-dimethyl-9-(2,6,6-trimethyl-1-cyclohexen-1-yl)-2,4,6,8-nonatetraenyl, 4,7,10,13-nonadecatetraenyl], $C_{8-30}$ alkynyl group [e.g. 9-octadecynyl, 9,15-octadecadiynyl, heptadecan-8-ynyl,4-decynyl], $C_{8-30}$ aralkyl [e.g. 15-(4-n-butylphenyl)pentadecyl, ω-(p-tolyl)heptadecyl, 6-(4-n-pentylphenyl)hexadecyl,15-phenylpentadecyl], and 15-(4-n-butylphenoxy)pentadecyl or 6-(4-n-pentylphenoxy)hexadecyl.

$R^2$, $R^3$ and $R^4$ are independently hydrogen or lower alkyl which may be substituted. As the lower alkyl group, there may be mentioned, for example, $C_{1-5}$ alkyl group (e.g. methyl, ethyl, propyl, i-propyl, n-butyl). These groups may further have one or more substituents such as hydroxycarbonyl, lower ($C_{1-3}$) alkoxycarbonyl, hydroxy, cyano or lower ($C_{1-3}$) alkoxy.

As the cyclic ammonio group represented by

there may be mentioned, for example, pyridinio, oxazolio, thiazolio, pyridazinio, quinolinio or isoquinolinio, and these groups may further have one or more substituents such as $C_{1-4}$ alkyl (e.g. methyl, ethyl), hydroxy, hydroxyethyl, aminoethyl, amino (imino), carbamoyl or ureido. The above-mentioned cyclic ammonio group includes cases where any two groups of $R^2$, $R^3$ and $R^4$ form a ring together with the quaternary nitrogen atom and the remaining one group is $C_{1-4}$ alkyl group (e.g. methyl, ethyl), for example, N-methylmorpholinio or N-methylpiperadinio.

The compound (I) may be present in, for example, the form of a salt representable by the formula

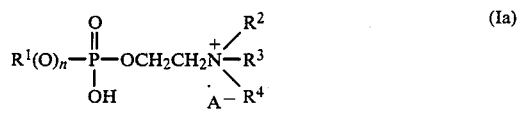
(Ia)

wherein $R^1$, $R^2$, $R^3$ and $R^4$ are as defined above and $A^-$ is an anion such as chlorine, bromine or iodine ion or by the formula

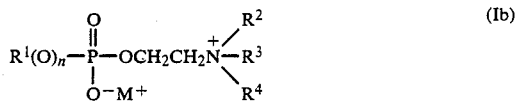
(Ib)

wherein $R^1$, $R^2$, $R^3$ and $R^4$ are as defined above, and $M^+$ is an alkali metal (e.g. Na, K) ion. The compound (I) can form a salt together with an alkaline earth metal (e.g. Ca, Mg) ion.

Further, this invention relates to novel phospholipids, inclusive of pharmaceutically acceptable salts thereof, of the formula

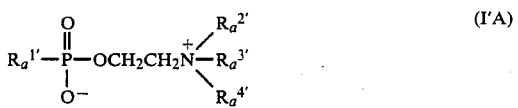
(I'A)

wherein $R_a^{1'}$ is a $C_{8-30}$ aliphatic hydrocarbon residue, and $R_a^{2'}$, $R_a^{3'}$ and $R_a^{4'}$ are independently hydrogen or lower alkyl or

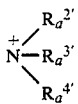

represents cyclic ammonio, and of the formula $$R_b{}^{1'}-O-\overset{O}{\underset{\underset{O^-}{|}}{P}}-OCH_2CH_2\overset{+}{N}\underset{R_b{}^{4'}}{\overset{R_b{}^{2'}}{\diagup}}R_b{}^{3'} \quad (I'B)$$

wherein $R_b{}^{1'}$ is a $C_{8-14}$ or $C_{18-30}$ aliphatic hydrocarbon residue, and $R_b{}^{2'}$, $R_b{}^{3'}$ and $R_b{}^{4'}$ are independently hydrogen or lower alkyl or $$\overset{+}{N}\underset{R_b{}^{4'}}{\overset{R_b{}^{2'}}{\diagup}}R_b{}^{3'}$$

represents cyclic ammonio.

Referring to the above formula (I'A), $R_a{}^{1'}$, $R_a{}^{2'}$, $R_a{}^{3'}$ and $R_a{}^{4'}$ are of the same meaning as $R^1$, $R^2$, $R^3$ and $R^4$ respectively.

Referring to the formula (I'B), the $C_{8-14}$ and $C_{18-30}$ aliphatic hydrocarbon residues represented by $R_b{}^{1'}$ include straight or branched chain saturated or unsaturated hydrocarbon residues having 8 to 14 and 18 to 30 carbon atoms. Practical embodiments of the aliphatic hydrocarbon residues are as exemplified in the foregoing and they may optionally have substituents as mentioned above.

$R_b{}^{2'}$, $R_b{}^{3'}$ and $R_b{}^{4'}$ are of the same meaning as $R^2$, $R^3$ and $R^4$ respectively.

The compounds (I'A) and (I'B) may be present in the form of salts corresponding to the salt (Ia) or (Ib).

Among the compounds of the formula (I), those wherein n equals to 1 can be produced by the following methods.

Method A

A compound of the formula $$R^1-OH \quad (II)$$

wherein $R^1$ is defined above, is allowed to react with a compound of the formula $$\underset{X}{\overset{X}{\diagdown}}\overset{O}{\underset{}{\overset{\|}{P}}}-OCH_2CH_2Y \quad (III)$$

wherein X and Y are respectively halogen (e.g. chlorine, bromine, iodine), to give a compound of the formula $$R^1O-\overset{O}{\underset{\underset{X}{|}}{\overset{\|}{P}}}-OCH_2CH_2-Y \quad (IV)$$

wherein $R^1$, X and Y are as defined above, which is then subjected to hydrolysis with water to give a compound of the formula $$R^1O-\overset{O}{\underset{\underset{OH}{|}}{\overset{\|}{P}}}-OCH_2CH_2-Y \quad (V)$$

wherein $R^1$ and Y are as defined above. This compound is allowed to react with a compound or a salt thereof of the formula $$N\underset{R^4}{\overset{R^2}{\diagup}}R^3 \quad (VI)$$

wherein each symbol is as defined above, to give the compound (I).

When two or more of $R^2$, $R^3$ and $R^4$ are hydrogen, the following Method B can also be employed.

Method B

A compound of the formula $$\underset{X}{\overset{X}{\diagdown}}\overset{O}{\underset{}{\overset{\|}{P}}}-OCH_2CH_2N\underset{R''}{\overset{R'}{\diagup}} \quad (III')$$

wherein X is as defined above, and either one of R' and R'' is —COOCH$_2$C$_6$H$_5$, —COOC$_6$H$_5$, —CHO, —COCF$_3$, —COCH$_2$C$_6$H$_5$, —Si(CH$_3$)$_3$ or —C(C$_6$H$_5$)$_3$ and the other one is $R^2$, or R' and R'', on cyclization with the adjacent nitrogen atom, form succinimido or phthalimido, is allowed to react with the compound (II). The reaction product is treated with water, then subjected to deprotecting reaction by a per se suitable conventional methods to give a compound $$R^1O-\overset{O}{\underset{\underset{O^-}{|}}{\overset{\|}{P}}}-OCH_2CH_2\overset{+}{N}H_2R^2 \quad (I''')$$

wherein $R^1$ and $R^2$ are as defined above.

The compounds (I) wherein n equals to 0 and 1 can both be produced also by the following method.

Method C

A compound of the formula $$R^1(O)_n\overset{O}{\overset{\|}{P}}(OH)_2 \quad (VII)$$

wherein $R^1$ and n are as defined above, is led to its reactive derivative, and then the reactive derivative is allowed to react with a compound of the formula $$HOCH_2CH_2\overset{+}{N}\underset{\underset{A^-}{R^4}}{\overset{R^2}{\diagup}}R^3 \quad (VIII)$$

wherein $R^2$, $R^3$ and $R^4$ are as defined above and $A^-$ is an anion such as chlorine, bromine, iodine or tosyl ion, to give the compound (I).

The material compounds for the above-mentioned reactions can all be easily produced by known methods or analogous methods thereof.

The reaction between (II) and (III) can be conducted in an inert solvent (e.g. benzene, toluene, dichloromethane, tetrahydrofuran) in accordance with a conventional manner in the presence or absence of a base (e.g.

a tertiary base such as pyridine, picoline, triethylamine). When the reaction is conducted in the presence of a base, the reaction temperature ranges from a temperature under ice-cooling to a room temperature. When the reaction is conducted in the absence of a base, the reaction temperature may be raised by heating in order to accelerate the reaction. Hydrolysis of (IV) is conducted by removing the solvent used for producing (IV) and adding water or by adding water to the reaction mixture as it is, which may, upon necessity, be heated up. For accelerating the hydrolysis, an inorganic base such as sodium hydrogen carbonate, sodium carbonate or sodium hydroxide may be added in accordance with a conventional manner.

(V) can be purified by means of chromatography, but it may be used for the subsequent reaction without purification.

The reaction between (V) and (VI) can be conducted in an inert solvent (e.g. benzene, toluene, tetrahydrofuran) or by using (VI) itself as the solvent. The reaction can be conducted at a temperature ranging from a room temperature to the boiling point of the solvent used, but when (VI) is a low-boiling point compound (e.g. trimethylamine), the reaction is preferably conducted in a sealed vessel. The objective compound (I) can be purified by a per se conventional methods such as a silicagel chromatography, recrystallization, or reprecipitation.

The reaction between (II) and (III') can be conducted in a manner analogous to that between (II) and (III). Removal of a protecting group may sometimes be accomplished by mere reaction with water in the presence of an acid or alkali, but it can be effected also by means of catalytic reduction or chemical reaction. For example, benzyloxycarbonyl group or trityl group can be removed by a catalytic reduction in a solvent (e.g. water, acetic acid, alcohol, tetrahydrofuran and a mixture thereof) in the presence of a catalyst (palladium-carbon, Raney nickel, platinum oxide, etc.) in accordance with a conventional manner. Succinimido group or phthalimido group can be removed by treating with hydrazine.

The method of leading (VII) to its reactive derivative in Method C can be conducted by a per se known method. For example, a method which comprises reacting (VII) with phosphorus pentachloride to lead to phosphoric chloride, or activating (VII) with a per se known condensing reagent (e.g. 2,4,6-trimethylbenzenesulfonyl chloride, 8-quinolinesulfonyl chloride, 2,4,6-isopropylbenzenesulfonyl imidazolide, 2,4,6-trimethylbenzenesulfonyl tetrazolide, dicyclohexyl carbodiimide, etc.), then by allowing (VIII) to react.

The compound (I'A) can be produced in accordance with Method C, and the compound (I'B) can be produced in accordance with Method A, B or C.

In addition to direct cytotoxicity to tumor cells, the compounds (I) and pharmaceutically acceptable salts thereof have host-mediated antitumor activity, though the mechanism has not yet been cleared. The compounds of the formula (I) wherein $R^1$ is a $C_{14-20}$ aliphatic hydrocarbon residue exhibit especially excellent effects. Specifically, when administered to animals bearing spontaneous carcinomas in mice or rats, carcinogen-induced solid tumors, MM46 derived from mastrocarcinoma, Ehrlich carcinoma, sarcoma 180, etc., or to nude mice implanted with human cancer cells, these compounds display life-span prolonging effects. The antitumor effect on sarcoma 180 and MM46 are respectively shown in Tables 1 and 2.

The antitumor agent of this invention displays excellent life-span prolonging effects in warm-blooded animals with a malignant tumor such as leukemia or solid tumor (e.g. digestive tract cancer or lung cancer). The compound (I) is generally available as a crystalline powder or a powder. Since it is sufficiently hydrophilic and lipophilic, the compound can be formulated into variety of pharmaceutical compositions such as injections, tablets, capsules, solutions, ointments, etc.

Injectable solutions and solutions for drip infusion, for instance, can be prepared in the conventional manner using physiological saline or an aqueous vehicle containing glucose and/or other auxiliaries. Tablets, capsules, etc. can also be prepared by the established pharmaceutical procedures. These preparations may take unit dosage forms for application by the routes of administration suited for the purposes e.g. intravenous or subcutaneous preparations or preparations for direct injection at an effected area in the case of injectable solutions. The dosage of the compound (I) for tumor-bearing warm-blooded animals is selected according to the clinical condition, route of administration, etc. and may generally range from about 0.1 to 100 mg/kg body weight or preferably from about 0.5 to 30 mg/kg body weight. The frequency of administration may be daily or at intervals of 2 to 7 days. For a sustained effective tissue concentration, the regimen of 1 to 3 divided doses daily or a drip infusion over a protracted time may also be feasible.

Further, the compound (I) has antimycotic activity. Its antimycotic spectrum covers Trichophyton, *Aspergillus niger*, Penicillium and yeasts and, therefore, the compound is of value in the treatment and prevention of diseases (e.g. trichophytia) of which these organisms are causative agents.

Such an antimycotic preparation can be produced by the established pharmaceutical procedure and while the relative amount of the active compound in the preparation is not particularly critical, the amount of the compound of this invention may range from about 0.01 to 70 weight % or preferably about 0.1 to 5 weight % of the total composition when the preparation is intended for the treatment of trichophytia for instance. Such an antimycotic preparation can be conveniently applied in the conventional manner, e.g. by direct coating or spraying to the affected site once to several times daily.

The compound (I) is also active against phytopathogenic pests, especially fungi and, therefore is useful as an agricultural fungicide for combating such plant diseases as rice blast, rice Helminthosporium leaf spot, rice stem rot, gray mold and cucumber anthracnose. The agricultural fungicides can be prepared in the conventional manner. The proper content of the active compound is generally about 1–90% for emulsifiable concentrates, wettable powders and the like, and about 0.1–10% for oil solutions, dusts and the like, and about 5–50% for granular preparations. Emulsifiable concentrates, wettable powders and the like are preferably sprayed after adequate dilution with water or the like (e.g. 50–5,000-fold dilution). These agricultural fungicides can be applied in the conventional manner and generally in a proportion of about 10 to 300 g as the active compound to each 10 ares of land. The concentration of the active component in such fungicidal preparations is about 10 to 1000 ppm.

The compound (I) of this invention is only sparingly active against bacteria in general and yet is active against protozoa (e.g. Tetrahymena), which activity in association with the aforesaid antifungal activity thereof makes the compound (I) of value as an antifungal/antiprotozoal agent for the assay of bacterial ecologies in the soil, activated sludge, body fluids, etc. The compounds of the formula (I) wherein $R^1$ is a $C_{12-16}$ aliphatic hydrocarbon residue have excellent actions mentioned above. Thus, for example, in isolating useful bacteria from the soil, or in detecting the activity of bacteria alone to the exclusion of protozoa and fungi for operation or analysis of the activated sludge process in waste water treatment, selective growth of bacteria is possible without allowing fungi and protozoa present in the sample to grow. Specifically, the test sample is added to a liquid or solid culture medium, then 0.1 ml of an aqueous solution of the compound (I) having a concentration of about 10 μg/ml to 100 mg/ml is added, and incubation is performed.

The following production examples, test examples and dosage form examples are further illustrative but by no means limitative of this invention.

PRODUCTION EXAMPLE 1

Tetradecyl 2-trimethylammonioethyl phosphate

Myristyl alcohol (5 g) and 2-bromoethyl phosphorodichloridate (9.02 g) were dissolved in benzene (40 ml). To the solution was added pyridine (2.95 g) dropwise. The mixture was stirred at room temperature for four hours. Then, the solvent was evaporated off. To the residue was added water, which was refluxed for one hour and half. The reaction mixture was cooled with ice, to which was added concentrated hydrochloric acid (6 ml). The mixture was subjected to extraction with chloroform. The extract was washed with water, dried and concentrated to dryness to give tetradecyl 2-bromoethyl phosphate, to which was added 20% toluene solution (60 ml) of trimethylamine. The mixture was left standing for five days, then concentrated to dryness. The residue was dissolved in methanol, to which was added silver carbonate (8.4 g). The mixture was refluxed for one hour and half, followed by filtration when hot. The filtrate was concentrated to dryness. The residue was purified by subjecting it to a silica-gel chromatography twice. [First: silica-gel, 70 g; eluent, methanol. Second: silica-gel, 70 g; eluent, chloroform-methanol-water=65:25:4 (by volume)]. The fractions containing the object compound were collected and reprecipitated from chloroform-acetone to give white powder (3.67 g).

IR(KBr)cm$^{-1}$: 3400, 2915, 2850, 1660, 1490, 1465, 1240, 1075, 970.

TLC: Rf=0.1 (silica-gel, CHCl$_3$—MeOH—H$_2$O, 65:25:4 (by volume)).

PRODUCTION EXAMPLE 2

Tetradecyl 2-pyridinioethyl phosphate

An analogous reaction to Production Example 1 was conducted by employing myristyl alcohol (5 g) and 2-bromoethyl phosphorodichloridate (9.02 g) to yield an intermediate compound, tetradecyl 2-bromoethyl phosphate. To this compound was added pyridine (25 ml), and the mixture was refluxed for one hour and half. The reaction mixture was left standing at room temperature overnight, followed by concentration to dryness. The residue was dissolved in methanol, to which is added silver carbonate (8.4 g). The mixture was refluxed for one hour and half, followed by filtration when hot. The filtrate was concentrated to dryness. The residue was purified subjecting it to a silica-gel chromatography twice. [First: silica-gel, 75 g; eluent, methanol. Second: silica-gel, 70 g; eluent, chloroform-methanol-water=65:25:4 (by volume)]. The fractions containing the object compound were collected and reprecipitated from chloroform and acetone to give the end-product as white powder. The yield was 3.65 g.

IR(KBr)cm$^{-1}$: 3400, 3050, 2920, 2850, 1630, 1490, 1235, 1080, 1049, 918, 778.

TLC: Rf=0.15 (silica-gel, chloroform-methanol-water, 65:25:4 (by volume)).

Elemental Analysis: $C_{21}H_{38}NO_4P \cdot 0.75H_2O$. Calcd.: C, 61.07; H, 9.64; N, 3.39; P, 7.50. Found: C, 60.91; H, 9.66; N, 3.68; P, 7.52.

PRODUCTION EXAMPLE 3

Oleyl 2-trimethylammonioethyl phosphate

An analogous reaction to Production Example 1 was conducted by employing oleyl alcohol (4.8 g) and 2-bromoethyl phosphorodichloridate (6.9 g) to yield 2.98 g of the object compound as hygroscopic white powder.

IR (liq) cm$^{-1}$: 3400, 2920, 2850, 1650, 1460, 1220, 1080, 963.

TLC: Rf=0.1 (silica-gel, chloroform-methanol-water, 65:25:4 (by volume)).

Elemental Analysis: $C_{23}H_{48}NO_4P \cdot H_2O$. Calcd.: C, 61.17; H, 11.16; N, 3.10; P, 6.86. Found: C, 61.31; H, 11.19; N, 2.93; P, 7.26.

PRODUCTION EXAMPLE 4

Oleyl 2-pyridinioethyl phosphate

An analogous reaction to Production Example 2 was conducted by employing oleyl alcohol (4.8 g) and 2-bromoethyl phosphorodichloridate (6.9 g) to yield 2.58 g of the object product as white powder.

IR(KBr)cm$^{-1}$: 3400, 2925, 2850, 1631, 1490, 1235, 1074, 780.

NMR(CDCl$_3$)δ: 0.90(3H), 1.26(22H), 1.87–2.20(4H), 3.48–4.63(6H), 4.93–5.50(4H, m), 7.96–8.65(3H, m), 9.51(2H, d, J=6 Hz).

Elemental Analysis: $C_{25}H_{44}NO_4P \cdot 1.5H_2O$. Calcd.: C, 62.48; H, 9.86; N, 2.91; P, 6.45. Found: C, 62.18; H, 9.82; N, 2.72; P, 6.55.

PRODUCTION EXAMPLE 5

Docosyl trimethylammonioethyl phosphate

1-Docosanol (3.26 g) and 2-bromoethyl phosphorodichloridate (2.53 g) were dissolved in a mixture of dichloromethane (6 ml) and carbon tetrachloride (3 ml), and the solution was stirred overnight. The reaction solution was refluxed for two hours, then the solvent was evaporated off. To the residue was added water (20 ml), which was refluxed for one hour. The reaction mixture, after cooling, was subjected to extraction with ether (70 ml). To the extract were added a given amount of BaSO$_4$ and water (2 ml). The mixture was stirred sufficiently, and the precipitating powder was collected by filtration. The power was dissolved in mixture of 3% hydrochloric acid (50 ml) and ether (50 ml) under vigorous stirring. The ether layer was taken, and the ether was evaporated off under reduced pressure. To the residue was added toluene (60 ml) containing trimethylamine (12 g). The mixture was heated at 60° C. in an autoclave for 48 hours. The reaction solution was concentrated to dryness under reduced pressure. The residue was dissolved in methanol (50 ml). To the solution was added silver carbonate (4.0 g), and the mixture was refluxed. The insolubles were removed by filtration. The filtrate was concentrated to dryness under reduced pressure. The residue was purified by means of chromatography using silica-gel (15 g). The product was subjected to re-precipitation from chloroform-acetone to give 1.30 g of the object compound as white powder.

IR(film)cm$^{-1}$: 3400, 2910, 2845, 1650, 1460, 1220, 1080, 1050, 960.

NMR(CDCl$_3$)δ: 0.67–1.67(43H), 3.33(9H), 3.57–4.67(6H, m).

Elemental Analysis: $C_{27}H_{58}NO_4P\cdot 4H_2O$. Calcd.: C, 57.61; H, 11.80; N, 2.49. Found: C, 57.62; H, 11.60; N, 2.61.

PRODUCTION EXAMPLE 6

Stearyl 2-trimethylammonioethyl phosphate

An analogous reaction to Production Example 1 was conducted by employing stearylalcohol (2.71 g) and 2-bromoethyl phosphorodichloridate (3.63 g) to give 1.32 g of the object compound as white powder.

IR(KBr)cm$^{-1}$: 2920, 2850, 1230, 1080.

NMR(CDCl$_3$)δ: 0.9(3H), 1.25(32H), 3.25(9H, s), 3.5–4.5 (6H, broad).

Elemental Analysis: $C_{23}H_{50}NO_4P\cdot 1.5H_2O$. Calcd.: C, 59.71; H, 11.55; N, 3.03; P, 6.69. Found: C, 59.93; H, 11.44; N, 3.02; P, 6.51.

PRODUCTION EXAMPLE 7

3,7,11,15-Tetramethylhexadecyl 2-trimethylammonioethyl phosphate

Dihydrophytol (0.60 g) and bromoethyl phosphorodichloridate (0.83 g) were dissolved in dry benzene (10 ml). To the solution was added dropwise dry pyridine (0.2 ml) under stirring. The mixture was stirred at room temperature for three hours, then cooled with ice, to which was added 2 ml of water. The mixture was again stirred vigorously at room temperature for two hours. The solvent was evaporated off, and the residue was dissolved in ether. The ether solution was washed with water, and then concentrated to dryness. The residue was dissolved in toluene (10 ml) containing trimethylamine (2 g), and the solution was left standing for five days. The reaction solution was concentrated under reduced pressure. The residue was subjected to a silica-gel chromatography (eluent, methanol) to yield 0.404 g (43%) of the object compound as colorless solid matter.

IR(film)cm$^{-1}$: 3350, 2850, 1460, 1380, 1225, 1080, 965.

NMR(90 MHz, CDCl$_3$)δ: 0.82, 0.87, 0.89(s, 15H), 1.20(m, 22H), 1.5(m, 2H), 3.38(s, 9H), 3.6–4.4(m, 6H).

Elemental Analysis: $C_{25}H_{54}NO_4P\cdot 0.5H_2O$. Calcd.: C, 63.53; H, 11.73; N, 2.96; P, 6.55. Found: C, 63.54; H, 12.07; N, 2.96; P, 6.31.

TLC Rf=0.26 (silica-gel, CHCl$_3$—MeOH—H$_2$O 65:25:4 (by volume)).

PRODUCTION EXAMPLE 8

(i) Cetylphosphonic acid

To ethyl phosphite (1.6 g) dissolved in 5 ml of tetrahydrofuran was added sodium (180 mg), and the mixture was dissolved. To this solution was added cetyl tosylate (514 mg), and the mixture was refluxed for ten hours. The reaction solution was concentrated to dryness under reduced pressure. To the residue was added water, which was acidified with concentrated hydrochloric acid, followed by extraction with ether and dried on Na$_2$SO$_4$. From the extract was removed the solvent by evaporation, and the residue was subjected to a silica-gel (7 g) chromatography. Fractions eluted with chloroform were collected and concentrated to dryness. To the residue was added concentrated hydrochloric acid (3 ml), which was refluxed for 18 hours. The resulting precipitates were collected by filtration, followed by recrystallization from n-hexane to give 240 mg (60%) of colorless needles.

IR(KBr)cm$^{-1}$: 2920(CH), 2850(CH), 1100(P=O).

Elemental Analysis: $C_{16}H_{35}O_3P$. Calcd.: C, 62.71; H, 11.51; P, 10.11. Found: C, 63.13; H, 11.76; P, 9.99.

(ii) 2-Trimethylammonioethyl cetyl phosphonate

Cetyl phosphonate (153 mg) and choline tosylate (0.5 g) are added to 4 ml of pyridine. The mixture was dissolved by heating at 50° C. To this solution was added trichloroacetonitrile (2 ml). The mixture was heated at 50° C. for 50 hours. One half volume of pyridine was evaporated off under reduced pressure. To the residue was added under stirring acetonitrile (20 ml). The resulting precipitates were collected to yield colorless powder (160 mg). The powder was dissolved in a mixture of tetrahydrofuran and water (7:3). The solution was poured onto a mixed resin (3 ml) of IRA410-Dowex 50W (2:1). The fractional eluate was concentrated to dryness under reduced pressure. The residue was subjected to a silica-gel (10 g) column chromatography using chloroform-methanol-water [65:25:4 (by volume)] as the eluent. The fractional eluates were collected and concentrated to dryness. The residue was recrystallized from chloroform-acetone to give 120 g (61%) of colorless needles.

IR(KBr)cm$^{-1}$: 2910(CH), 2850(CH), 1465(CH$_2$), 1200(P=O), 1190(P=O), 1077, 1045, 960.

PRODUCTION EXAMPLE 9

3,7,11-Trimethyldodecyl 2-trimethylammonioethyl phosphate

In 10 ml of benzene was dissolved 1.0 g (4.38 mmol) of 3,7,11-trimethyl-1-dodecanol. To the solution, while cooling with ice, were added 1.80 g (4.38 mmol×1.7) of 2-bromoethyl phosphorodichloridate and 0.59 g (4.38 mmol×1.7) of pyridine. The mixture was stirred for 2.5 hours at room temperature, to which was added 2 ml of water, followed by vigorous stirring for further 2.5 hours. The reaction solution was concentrated, and the residue was subjected extraction with ether. The ether extract was washed with water, then the solvent was evaporated off. The residue was dried and dissolved in 10 ml of toluene containing 2 g of trimethylamine, then the solution was left standing for four days. The reaction was concentrated to dryness. The residue was subjected to a silica-gel chromatography [first eluent: methanol, second eluent: chloroform-methanol-water (65:25:4 by volume)] to give 0.57 g (34%) of the object compound as colorless solid.

TLC Rf=0.2(CHCl$_3$—MeOH—H$_2$O 65:25:4 (by volume)).

IR(film) cm$^{-1}$: 3390, 2955, 2870, 1460, 1380, 1230, 1085, 970.

NMR(90 MHz, CDCl$_3$)δ: 0.82, 0.89(s, 12H), 1.0–1.7(m, 18H), 3.40(s, 9H), 3.6–4.1(br. 4H), 4.1–4.5(br. 2H).

Elemental Analysis: C$_{20}$H$_{44}$NO$_4$P·1.5H$_2$O. Calcd.: C, 57.12; H, 11.26; N, 3.33; P, 7.36. Found: C, 56.99; H, 11.20; N, 3.59; P, 7.34.

PRODUCTION EXAMPLE 10

(E)-2-Octadecenyl 2-trimethylammonioethyl phosphate (E)-2-Octadecen-1-ol (1.34 g, 5 mmol) and 2-bromoethyl phosphorodichloridate (1.57 g, 6.5 mmol) were dissolved in benzene (25 ml). To the solution was added a solution of pyridine (514 mg, 6.5 mmol) in benzene (2.5 ml) dropwise. The mixture was stirred at room temperature for four hours. Then, the solvent was evaporated off. To the residue was added water (50 ml), which was refluxed for one hour and half. After cooling, the mixture was extracted with chloroform. The extract was dried and concentrated to dryness to give (E)-2-octadecenyl 2-bromoethyl phosphate, to which was added 20% toluene solution (40 ml) of trimethylamine. The mixture was left standing for 66 hours, then concentrated to dryness. The residue was subjected to a silica-gel column chromatography using methanol as an eluent to give 0.5 g (23%) of the object compound as colorless powder.

IR(KBr)cm$^{-1}$: 2920, 2850, 1472, 1240, 1100, 1025, 971.

NMR(90 MHz, CDCl$_3$)δ: 0.87(3H), 1.24(26H), 1.82–2.12(2H), 3.33(9H, N$^+$Me$_3$), 3.65–3.80(2H), 4.05–4.43(4H), 5.45–5.70(2H).

Elemental Analysis: C$_{23}$H$_{48}$NO$_4$P·0.75H$_2$O. Calcd.: C, 61.78; H, 11.16; N, 3.13; P, 6.93. Found: C, 61.77; H, 11.75; N, 3.11; P, 6.94.

PRODUCTION EXAMPLE 11

(1-Octyl)nonyl 2-trimethylammonioethyl phosphate

9-Heptadecanol (2.56 g, 10 mmol) and bromoethyl phosphorodichloridate (4.11 g, 17 mmol) were dissolved in dry benzene (20 ml). To the solution was added dropwise dry pyridine (1.34 g, 17 mmol) under stirring. The mixture was stirred at room temperature for three hours, then to which was added water. The mixture was again stirred for thirty minutes at 80° C.

The solvent was evaporated off, and the residue was dissolved in ether. The ether solution was washed with water, and then concentrated to dryness. The residue was dissolved in toluene (25 ml) containing trimethylamine (5 g), and the solution was left standing for three days.

The reaction solution was concentrated under reduced pressure. The residue was subjected to a silica-gel chromatography [eluent: chloroform-methanol-water (65:25:4 by volume)] to yield 0.76 g of the object compound as colorless solid matter.

IR(KBr)cm$^{-1}$: 2925, 2860, 1465, 1380, 1230, 1085, 970, 760.

NMR(90 MHz, CDCl$_3$)δ: 0.87(t, 6H), 1.24(m, 28H), 3.37(s, 9H), 3.79(br, 2H), 4.0–4.4(br, 3H).

Elemental Analysis: C$_{22}$H$_{48}$NO$_4$P·0.5H$_2$O. Calcd.: C, 61.37; H, 11.47; N, 3.25; P, 7.19. Found: C, 61.59; H, 11.68; N, 3.37; P, 7.26.

TEST EXAMPLE 1

Effects against sarcoma 180

To a group of ICR mice was administered intraperitoneally 1 mg of the test compound dissolved in 0.2 ml of physiological saline per mouse. Four days later, 1×10$^5$ cells of sarcoma 180 per mouse were administered intraperitoneally. The survival rates (T/C) of the test group to the control group administered with only physiological saline were assayed. The results are as shown in Table 1.

TABLE 1

| Effects against sarcoma 180 | |
|---|---|
| Test Compound | Survival Rate (T/C) |
| Production Example 1 | 217 |
| Production Example 2 | 152 |
| Production Example 3 | 302 |
| Production Example 4 | 308 |
| Production Example 5 | 167 |
| Production Example 6 | 200 |
| Production Example 11 | 282 |

TEST EXAMPLE 2

Effects against MM46

To each of C3H/He mice group was transplanted intraperitoneally 1×10$^4$ cells of MM46 carcinoma. Four times from five days to two days before the transplantation and four times from two days to five days after the transplantation, eight times in total, 250 μg of the test compound dissolved in 0.2 ml of physiological saline was administered intraperitoneally. The number of mice surviving on the 24th day after transplantation of the carcinoma cells was compared with that of the control group administered with saline. The results are as shown in Table 2.

TABLE 2

| Effects against MM46 | |
|---|---|
| Test Compound | Surviving mice/Test mice |
| Physiological saline (control) | 0/5 |
| Production Example 3 | 3/5 |
| Production Example 4 | 2/5 |

TEST EXAMPLE 3

The antifungal and antiprotozoal activities of the compounds of this invention are as shown in Tables 3 and 4 respectively.

The antimycotic (antifungal) activity values as shown in Table 3 were assayed on various organisms including phytopathogenic microorganisms using 1% glucose-bouillon agar medium, and the minimum inhibitory concentration (MIC) was determined by the serial dilution method.

The antiprotozoal activity values as shown in Table 4 were assayed using *Tetrahymena pyriformis* W strain as the test organism and an assay medium composed of 20 g of tryptose peptone (manufactured by Difco), 1 g of yeast extract, 2 g of glucose, 1000 ml of distilled water and 10 ml of 1M phosphate buffer (pH 7.0). The incubation was continued at 28° C. for 44 to 48 hours and the minimum inhibitory concentration (MIC) of the compounds of this invention was determined by the broth dilution method.

TABLE 3

Antifungal Activity [MIC (μg/ml)]

| Production Example No. | Test Organism | | | | | | | | |
|---|---|---|---|---|---|---|---|---|---|
| | 1 | 2 | 3 | 4 | 5 | 6 | 7 | 8 | 9 |
| 1 | 12.5 | 6.25 | 12.5 | 3.12 | 12.5 | 25 | 25 | 6.25 | 3.12 |
| 2 | 25 | 12.5 | 50 | 3.12 | 25 | 25 | 50 | 12.5 | 3.12 |
| 3 | 12.5 | 25 | 6.25 | 1.56 | 12.5 | 12.5 | 3.12 | 1.56 | 50 |
| 4 | 50 | 25 | 25 | 3.12 | 50 | 25 | 6.25 | 6.25 | 50 |
| 6 | 25 | 25 | 12.5 | 6.25 | 50 | 50 | 6.25 | 3.12 | 100 |
| 7 | — | — | — | 1.56 | — | 6.25 | 25 | ND | 100 |

| Test Organism | | |
|---|---|---|
| 1. | Aspergillus niger | IFO-6341 |
| 2. | Penicillium citrinum | IFO-6352 |
| 3. | Saccharomyces cerevisiae | IFO-0209 |
| 4. | Pyricularia oryzae | IFO-5279 |
| 5. | Helminthosporium oryzae | IFO-7503 |
| 6. | Gibberella fujiknroi | |
| 7. | Botrytis cinerea | IFO-5365 |
| 8. | Helminthosporium sigmoideum | IFO-4867 |
| 9. | Colletctrichum lagenarium | IFO-6207 |

TABLE 4

MIC (μg/ml) against *Tetrahymena pyriformis* W strain

| Production Example No. | MIC |
|---|---|
| 1 | 2 |
| 2 | ≧4 |
| 3 | 0.4 |
| 4 | 2~4 |
| 5 | >4 |
| 6 | ≦1 |
| 7 | 4 |
| 8 | 2 |
| 10 | ≦1 |
| 11 | ≦1 |

DOSAGE FORM EXAMPLE 1

Oleyl 2-trimethylammonioethyl phosphate (80 g) is dissolved in 1 liter of distilled water, the solution is passed through a sterilization filter, poured into 1,000 vials (1 ml per vial) and lyophilized, and the vials are tightly stoppered.

Separately, a solution containing xylitol or mannitol (100 g in 2 liters) in distilled water for injection is poured into 1,000 ampules for injectable solution (2 ml per ampule) in an aseptic manner, and the ampules are sealed by fusing.

For administration, the powder in one vial is dissolved in the above-mentioned xylitol (or mannitol) solution in one ampule.

DOSAGE FORM EXAMPLE 2

Tablets, each weighing 370 mg and having a diameter of 9.5 mm, are prepared in a conventional manner by mixing the ingredients:

| (1) | Oleyl 2-pyridinioethyl phosphate | 100 mg per tablet |
| (2) | Lactose | 200 mg per tablet |
| (3) | Corn starch | 51 mg per tablet |
| (4) | Hydroxypropylcellulose | 9 mg per tablet | followed by granulation, addition of corn starch (8 mg per tablet) and magnesium stearate (2 mg per tablet) and tableting.

DOSAGE FORM EXAMPLE 3

Tablets containing tetradecyl 2-trimethylammonioethyl phosphate are prepared in the same manner as in Dosage Form Example 2, and coated with a solution of hydroxypropylmethylcellulose phthalate (14 mg per tablet) and castor oil (1 mg per tablet) in an acetone-ethanol (4:6) mixture, the concentration of the solutes being 7%. Thus are obtained enteric coated tablets.

What is claimed is:

1. The compound oleyl 2-pyridinioethyl phosphate.

* * * * *